United States Patent [19]

Diesel

[11] 4,346,609
[45] Aug. 31, 1982

[54] FLUID SAMPLING DEVICE

[75] Inventor: Hans A. Diesel, New Malden, England

[73] Assignee: Exxon Research & Engineering Co., Florham Park, N.J.

[21] Appl. No.: 200,387

[22] Filed: Oct. 24, 1980

[30] Foreign Application Priority Data

Nov. 6, 1979 [GB] United Kingdom ............... 7938332

[51] Int. Cl.³ ............................................. G01N 1/14
[52] U.S. Cl. ............................ 73/863.33; 73/863.51; 73/863.84
[58] Field of Search ........... 73/863.02, 863.31, 863.33, 73/863.84, 864.34

[56] References Cited

U.S. PATENT DOCUMENTS 2,906,126  9/1959  Brown ................................. 73/422
3,031,890  5/1962  Struck ................................. 73/422
3,218,866 11/1965  Struck ................................. 73/422

FOREIGN PATENT DOCUMENTS

1026905  9/1964  United Kingdom .

Primary Examiner—S. Clement Swisher
Attorney, Agent, or Firm—Donald F. Wohlers

[57] ABSTRACT

A device for taking fluid samples from one or more locations in a pipeline or vessel comprises a hollow body (31) for projection into the pipeline or vessel, a rotatable internal sleeve (50) having fluid inlet ports (53) which are in register with respective inlet ports (35) in the body (31) at least once per revolution, for fluid to enter a cylinder (70) which is within the sleeve (50), and fixed relative to the body (31). A piston (120) is moved in the cylinder in accordance with the profile of a cam groove (60) formed in the internal wall of the sleeve (50), and executes a fluid sample discharge stroke when the rotation of the sleeve (50) brings into register a fluid discharge port (74) of the cylinder, a fluid discharge port (57) of the sleeve and a fluid discharge port (38) of the body (31). The device provides reliable sampling for most fluids and over a very wide range of conditions.

20 Claims, 26 Drawing Figures

FLUID SAMPLING DEVICE

The present invention relates to a fluid sampling device operable to provide samples of fluid from within a pipeline or vessel.

By "fluid" is meant any flowable substance such as gases, liquids and flowable semi-solid materials.

In U.K. Pat. No. 1,026,905 there is described and claimed a fluid sampling device for withdrawing measured samples from a flow line and comprising a sleeve member projecting into said flow line and provided with two opposed radial ports, a delivery tube connected to said sleeve member, a cup member within said sleeve member in coaxial relationship, means for rotating one of said members and preventing rotation of the other member, said cup member being provided with two opposed radial ports movable into register with the radial ports in the sleeve member during each 180° rotation between the two members, said sleeve member having a longitudinal port for establishing communication between the delivery tube and the sleeve member, said cup member having a longitudinal port for register with the longitudinal port in the sleeve member to establish communication between the cup member and the delivery tube, said longitudinal ports being movable into register with each other during each 360° rotation between the members when the radial ports in the sleeve member and cup member are out of register, a piston in said cup member for expelling fluid samples through said longitudinal ports to the delivery tube, means for reciprocating the piston, and cam means on the sleeve member and piston for effecting retraction of the piston.

As described, the movement of the piston in one direction is caused by the cam means on the sleeve member, and movement in the opposite direction is caused by the effect of fluid pressure in the fluid line in a direction tending to impart a fluid expelling stroke to the piston and which is effective to move the piston only when the said longitudinal ports are in register with each other.

The sampling device as described in the foregoing patent specification is not suited to practical situations since for a large part of the operating cycle, the position of the piston relative to the cup member is not determined by any physical constraint and the expulsion of fluid is conditional upon there being an adequate pressure drop for expulsion to occur. If there should be an excessive head of liquid and/or fluid friction and/or a slight obstruction (e.g. due to debris) between the entrance to the longitudinal port of the cup member and the sample exit from the delivery tube, the volume of the sample may be inadequate or there may be no sample expelled from the delivery tube exit. Moreover, during operation of the device at relatively high speeds, it has been observed that the foregoing problems are exacerbated because the inertia of the fluid sample trapped in the cup member reduces the amount of the sample which can be expelled in the time between one fluid expulsion stroke and the next one. It has also been observed that the foregoing problems are more acute when a relatively viscous fluid, such as a heavy crude oil, is being sampled by the device.

In order to mitigate the foregoing practical difficulties, sampling devices in accordance with U.K. Pat. No. 1,026,905 have been modified by the provision of compression springs to maintain a cam follower pin engaged with the piston pressed against a cam profile formed on the edge of the sleeve member at the opposite axial end to the longitudinal port therein. However, this expedient has not proved satisfactory in practice since at relatively high operating speeds, piston chatter has been observed leading to unreliable sampling, and the problems arising from the inertia and viscosity of the fluid sample are only slightly reduced but not eliminated.

A further defect of the fluid sampler of U.K. Pat. No. 1,026,905 and the modified version described above is that the piston must abut against the closed end of the cup member to ensure complete expulsion of the sample, and from the mechanical design point of view, the contact between the piston face and the closed end of the cup is unsatisfactory and has been found to cause damage. Moreover, the piston face carries a frusto-conical protrusion which is intended to register in and close the longitudinal port in the closed end of the cup until the longitudinal port in the sleeve member is out of register therewith to prevent the backflow of the expelled sample. This check valve arrangement has been found to be unsatisfactory in practice since the protrusion has had to be formed from a pliant material to accommodate for inaccuracies of alignment thereof with the longitudinal port in the closed end of the cup, but such pliant material has been found to wear and/or fail, particularly over long periods of use and over shorter periods when a fluid containing suspended solids is being monitored.

Since the purpose of a fluid sampling device is to provide samples which are of substantially uniform volume over relatively long periods of time with high reliability, it has been apparent for some time that a new approach to providing a fluid sampling device is required, and having regard to the foregoing, the present invention provides a fluid sampling device which, when assembled, comprises: a cylindrical sample receptacle having one end closed and the other end open, a sample entrance port in the cylindrical side of the receptacle, a sample discharge port for the discharge of samples of fluid from the interior of the receptacle; a piston reciprocable in the receptacle; a cam follower associated with the piston so that the follower and the piston move together, the cam follower having a part protruding through a slot in the cylindrical wall of the receptacle; a cylindrical sleeve in which the receptacle is received for relative rotation of the receptacle and sleeve; the sleeve having a sample entrance port which is arranged to be fully in register with the sample entrance port of the receptacle at a selected relative rotational position of the sleeve and the receptacle; the sleeve having an internal cam profile groove in which the protruding part of the cam follower is received and engaged by the sides of the groove to cause reciprocation of the piston in the receptacle during relative rotation of the sleeve and receptacle; a hollow body in which the cylindrical sleeve is retained for relative rotation between the sleeve and the body; the body having a sample entrance port which is arranged to be fully in register with the sample entrance ports of the sleeve and the receptacle at a selected relative rotational position thereof; and means preventing relative rotation between the hollow body and the receptacle; the arrangement and construction of the device being such that the said sample entrance ports are fully in register when the piston is positioned by the engagement of the follower and the cam profile groove substantially at the bottom of its reciprocating stroke relative to the position of the sample discharge port, and such that at least the sample entrance ports of the receptacle and sleeve are fully out of register when the piston is positioned nearer to the sample discharge port than the bottom of its reciprocating stroke, whereby on relative rotation of the sleeve and the receptacle, the movement of the piston towards the top of its stroke causes any contents of the receptacle to be expelled via the sample discharge port.

In the device of the invention, the position and displacements of the piston in the receptacle are determined by the interaction of the cam follower and the cam profile groove, and as a result, the volume of sample discharged from the receptacle is always substantially the same during one operating cycle as during every other operating cycle, irrespective (within reasonable practical limits) of the speed of relative rotation of the sleeve and receptacle and of the viscosity of the fluid.

Preferably, the receptacle, sleeve and body each have an exit port formed substantially diametrically opposite the respective sample entrance ports whereby when said sample entrance ports are all at least partially in register with each other, fluid outside the device can pass into the receptacle through the sample entrance ports and then out via the exit ports, whereby the fluid in the receptacle is substantially identical with the fluid outside the device in the vicinity of the entrance and exit ports.

In a preferred embodiment, the sample discharge port is at the end of a radial bore in the cylindrical sample receptacle, and the sleeve and body have corresponding sample discharge orifices which are arranged to be in register with the sample discharge port when the position of the cam follower in the cam groove corresponds with that of the piston moving from the bottom to the top of its stroke. As a result of this arrangement, fluid can be discharged from the receptacle on displacement of the piston only when all the said discharge orifices and discharge port are in register with each other. When the discharge port and orifices are not in register, no fluid sample movement into or out of the receptacle can take place, and in consequence, it is unnecessary for the great majority of practical uses to provide a check valve to prevent the return of at least part of a previously discharged sample back into the receptacle, and even if such a check valve were found to be useful or necessary, it would not be associated with the piston, as it is in the device described in U.K. Pat. No. 1,026,905, but would be a conventional check valve disposed at a suitable location in the samples-discharge path outside the receptacle.

Preferably, there is provided a duct for receiving samples discharged from the sample discharge port via the said sample discharge orifices. Such a duct would provide at least part of the said samples-discharge path.

Preferably, the form of the cam groove is such that the piston is substantially stationary at, or moving relatively slowly towards, the bottom of its stroke when the sample entrance ports of the receptacle, sleeve and body are all at least partly in register with each other. This feature ensures that fluid enters the receptacle at least partially as a result of its fluid energy rather completely than as a result of being aspirated by movement of the piston.

Preferably the device has at least one orifice to permit the ingress and egress of fluid behind the piston during movement thereof. The purpose of each an orifice is to prevent the build-up of fluid pressure ehind the piston which might cause an increase in the power required to maintain operation of the sampling device.

When samples are required from a relatively extensive container or pipeline in order to evaluate the composition and/or quality of fluid at different locations therein, it is preferred to employ a device comprising a plurality of similar cylindrical sample receptacles coaxially received as a stack within the sleeve and rotationally fixed relative to each other, each receptacle having a piston reciprocable therein and each piston having associated therewith a cam follower whereof a part protrudes through a respective slot in the cylindrical wall of the receptacle and is engaged against the sides of a respective cam profile groove whose form is such as to cause reciprocation of the respective piston in the receptacle on relative rotation of the sleeve and receptacles, each receptacle having a sample entrance port corresponding with the sample entrance port of each receptacle, the sleeve and receptacles being coaxially received in the body, the body having a sample entrance port corresponding with the sample entrance port of each receptacle, the body and sleeve being arranged for relative rotation and there being means preventing relative rotation between the body and the receptacles, there being sample discharge ports for the discharge of samples from each receptacle and respective corresponding sample discharge orifices in the sleeve and body, the construction and arrangement of the device being such that for each receptacle, the cam follower and cam profile groove maintain the piston at the bottom of its stroke when the corresponding sample entrance ports of the receptacle, sleeve and body are all at least partly in register with each other, and cause the piston to move towards the top of its stroke when the corresponding discharge orifices are at least partly in register with each other.

Preferably, the profiles of the cam grooves are of such form that the piston in each receptacle is substantially in the same position in its working cycle as the piston in every other receptacle.

The device preferably comprises respective ducts for receiving samples discharged from each of the sample discharge ports.

In preferred embodiments, the device comprises a spacing member between and abutted by two axially separated receptacles, the or each spacing member having a lug at one axial end which is received in a corresponding recess in an abutting receptacle to prevent relative rotation of the said two receptacles.

The other axial end of the spacing member may have a recess in which a lug of an abutting receptacle is received to prevent relative rotation of the spacing member and receptacle.

The device may comprise spring means which biasses all said receptacles towards one axial end of the sleeve.

The said means preventing relative rotation of the body and the receptacles may comprise a keying member which connects one axial end of the body and an adjacent part of the receptacle at that axial end of the device, and the keying member may comprise a thrust plate member, the spring means being maintained in compression between the thrust plate member and the receptacle at the opposite axial end of the sleeve.

The sample entrance ports are preferably located along the length of the device with a spacing in accordance with a mathematical samples' averaging technique, e.g., the so-called Chebyshef averaging method.

The device preferably comprises a shaft attached to the sleeve and has a part protruding through an axial end of the body for attachment to means for rotating the shaft.

The invention also provides a pipeline or container in which a sampling device as described above is installed, and further provides an installation comprising such a pipeline or container and means for rotating the sleeve.

The invention is now further described with reference to non-limitative examplary embodiments thereof and with reference to the accompanying drawings, in which.

Figure 1:
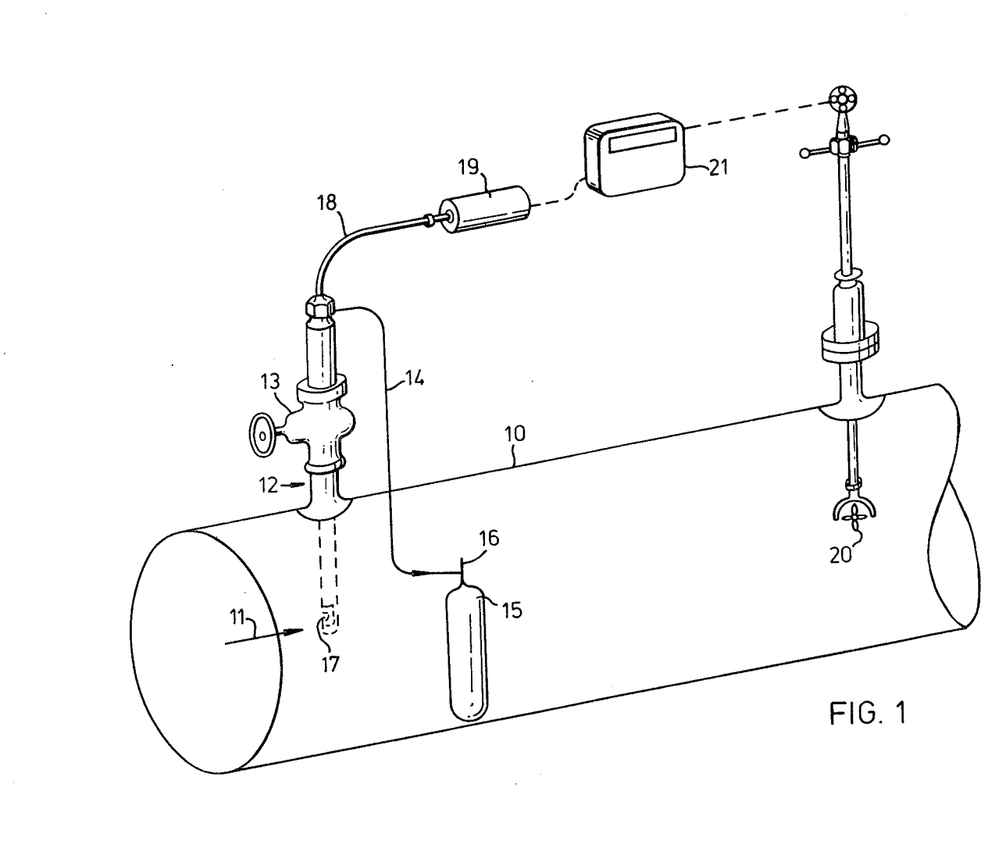
FIG. 1 is a schematic drawing to illustrate equipment employed in sampling crude oil flowing in a pipeline.

Referring first to FIG. 1, the pipeline is indicated by reference 10 and the direction of flow of the crude oil is indicated by arrow 11. A sampling device or sampler 12 protrudes into the interior of the pipeline 10 through a valve 13 and is connected by tube 14 to a sample receptacle 15 having a vent 16 provided with a relief valve (not shown) set to open at a selected pressure. The sampler 12 which is illustrated has a single inlet-port 17 and comprises a rotatable sleeve valve (not shown) which can be rotated to close the port 17 and define a cylinder in which a sample of oil from port 17 is trapped, there being a cam operated piston (not shown) which displaces the sample out of the cylinder into the tube 14. The rotation of the valve and cam are both effected by a flexible connection 18 from a suitable motor 19 (e.g. an air motor), and the speed of rotation is arranged to be proportional to the flow rate of oil, the latter being determined by a suitable flow-meter, e.g. a small turbine 20, which senses the flow-rate of oil and transmits a corresponding signal directly or indirectly to a flow proportional controller 21 which controls the speed of the motor 19 so that it is proportional to the flow-rate as sensed by and transmitted from the flow-meter, e.g. the turbine 20.

Figure 2A:
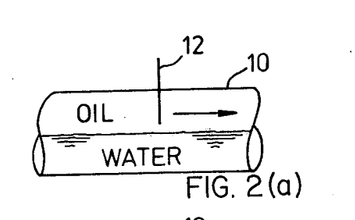
FIG. 2(a)–2(f) schematically shows different flow regimes and types of flow of crude oil and water in a pipeline in which a sampling device is installed.
Figures 2B, 2E:
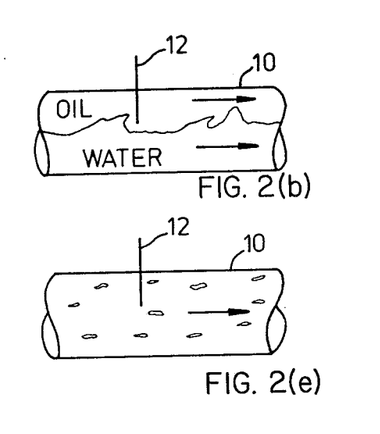
Figure 2C:
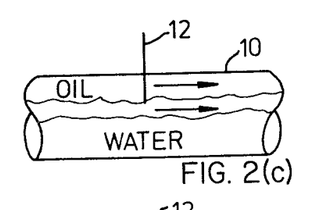
Figure 2D:
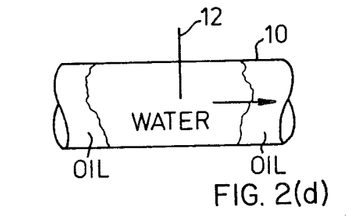
Figure 2F:
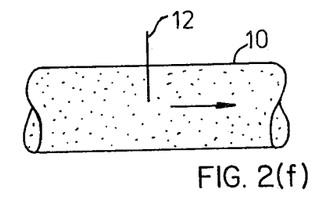

Crude oil often contains contaminants, and the more important of these are water (often containing dissolved salts) and solids and sediment (such as e.g. waxes, sand and other solids). If the crude oil is being pumped through the pipeline 10 from a storage tank (e.g. a cargo compartment of a marine tanker), the water and sediment content of the oil will vary depending on whether the oil is being pumped from the bottom of the tank, where water and sediment tend to accumulate to the greatest degree, or from elsewhere. Moreover, not only does the water and sediment content vary, but the degree and/or manner of its dispersion in the oil will vary depending on the amount of turbulence at particular locations in the pipeline 10. FIG. 2 shows a number of commonly-encountered situations for crude oil passing through the pipeline 10 and the manner in which the single port sampler 12 can provide misleading or inaccurate samples of the crude oil passing through the pipeline 10. In FIG. 2(a), the water forms a layer under the oil with the interface below the single inlet port (not indicated) at the bottom of the sampler 12. It can readily be appreciated that the sampler will provide samples in the receptacle 15 (FIG. 1) which are not at all representative of the oil-water mixture in the pipeline. The situation in FIG. 2(a) is most likely to be found when no pumping is taking place and/or at very low pumping speeds. FIG. 2(b) depicts the situation at a higher pumping speed when the oil-water interface is disturbed by shearing, but it is apparent that the samples from sampler 12 will contain only a minor proportion of the actual water present in the pipeline 10. At a still higher flow rate, shown in FIG. 2(c), the water and oil at the interface are sheared to the extent that immediately below the top layer consisting of substantially water-free oil, is a mixture of oil and water, below which is a layer of substantially oil-free water. As shown in FIG. 2(c), the bottom of sampler 12 is too high to receive representative samples of the central oil-water layer, and even if it were lower, it would not necessarily receive oil-water samples truly representative of the mixture passing through the pipeline 12. FIG. 2(e) shows the greater and more uniform dispersion of water in the oil at still higher pumping rates, but the water tends to be in the form of relatively large lenses or globules which militate against accurate sampling by the sampler 12. FIG. 2(f) shows a regime in which the water is uniformly dispersed as small droplets suspended in the oil. In this regime, the samples from sampler 12 may be likely to be substantially representative of the composition of the oil in the pipeline 10. It will be appreciated from the foregoing that the accuracy of sampling by the sampler 12 depends on the degree of turbulence and uniform relative dispersion of the oil and water phases as they approach and pass the sampler 12 and also on the depth of insertion of the bottom of the sampler 12 into the pipeline 10. The turbulence is affected by the pumping rate, the oil viscosity, the configuration of the pipeline 10 and any turbulence-creating obstacles therein, inter-alia, and the separation of the water from the oil can also be affected by the pumping machinery (e.g., centrifugal pumps which may tend to promote separation) and the length of the pipeline. FIG. 2(d) shows a plug of water passing through the pipeline 10. Such a plug can be accurately sampled if it is not so short that it passes the sampler 12 while its inlet port is closed.

It will be appreciated from the foregoing that a sampler having a single sample entry port may give a misleading sample of a fluid passing through a pipeline even when the sampler is working efficiently and reliably. However, it will also be apparent that there may be circumstances in which the samples provided by a single-ported sampler may not be misleading, provided that the sampler is operating efficiently and reliably, and the water-oil dispersion is uniform across the pipeline cross-section.

Figure 3:
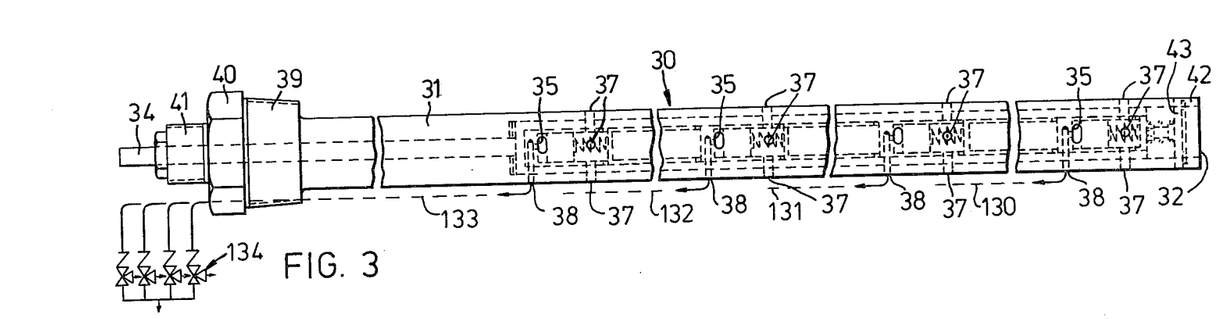
FIG. 3 is an external view of one embodiment of a fluid sampling device of the invention, with some internal parts thereof shown in dotted lines, and some external parts thereof shown diagrammatically.
Figure 4:
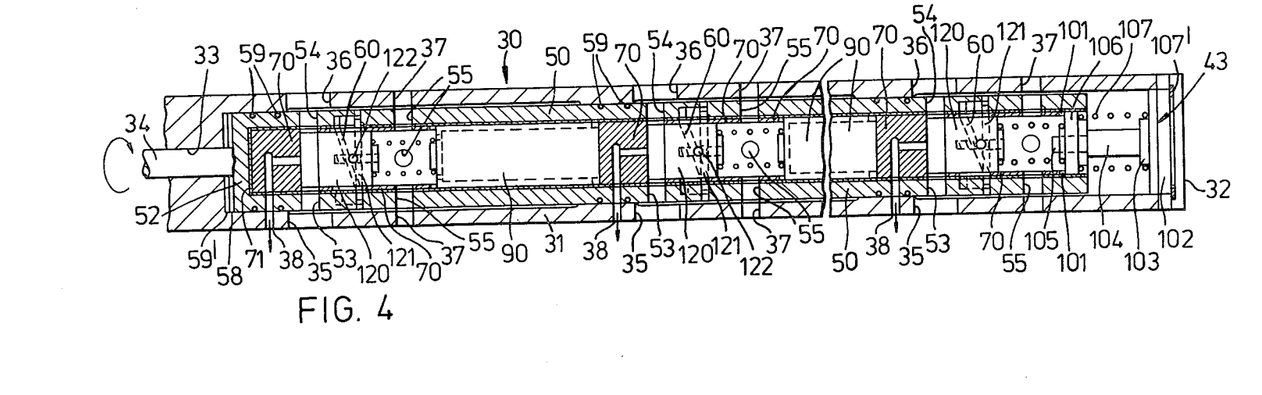
FIG. 4 is a cross-section view in an axial plane of part of the device of FIG. 3, to a larger scale in which the relative positions of some features are changed for clarity of illustration.

Reference is now made to FIGS. 3 and 4 which show a sampler having four sample inlet ports and which is generally indicated by reference 30.

The sampler 30 comprises a hollow, cylindrical outer body 31 which is open at one end 32 and closed adjacent to the other end except for an axial bore 33 for rotatably receiving a drive shaft 34. The body 31 has four axially spaced-apart radial inlet ports 35 (of which only three are shown in FIG. 4), all of which are defined between an common pair of axial planes so that they are all in line along one side of the body 31. Diametrically opposite each of the inlet ports 35 are exit ports 36 for the flow of crude oil from one side of the body 31 and through the body 31 to the other side via the inlet ports 35 and the exit ports 36 when the other parts of the sampler 31 are relatively so located to permit such through flow. For the sake of clarity of illustration, the ports 35 of FIG. 3 are shown at right angles to their true positions in FIG. 4. As a result, the ports 35 and 36 appear to be aligned with other ports, mentioned below, in FIG. 4.

The body 31 is additionally formed with diametrically opposed quartets of pressure equalization ports 37, of which at least a pair from each quartet is preferably (but not necessarily) in the same axially-disposed alignment as the ports 35 and 36.

The number of diametrically opposed quartets of ports 37 are equal in number to the number of pairs of ports 35, 36 and each spaced apart from a respective port pair 35, 36 by suitable, e.g. selected equal, distances. There are also formed radial sample discharge ports 38 in a number equal to the number of ports 35. Preferably (but not essentially), the ports 38 are on the same side of the body 30 as the ports 35 and have their central axes in the same radial plane as the ports 35.

At the axially closed end of the body 31 is provided a tapered externally threaded boss 39 and an adjacent integral nut 40 for fastening and sealing the body 31 and hence the sampler 30 relative to a pipeline somewhat in the manner depicted in FIG. 1 wherein the sampler 12 is fastened to, and seated with, the top end of an insertion pipe containing the valve 13. The axially closed end of the body 31 is also provided with a threaded end portion 41 which forms a stuffing box or component thereof to permit rotation of the shaft 34 substantially without fluid leakage out of the sampler 30.

At the axially open end, the body 31 has a pair of diametrically opposed slots 42 to receive part of a key member, generally indicated by reference 43.

Figure 6:
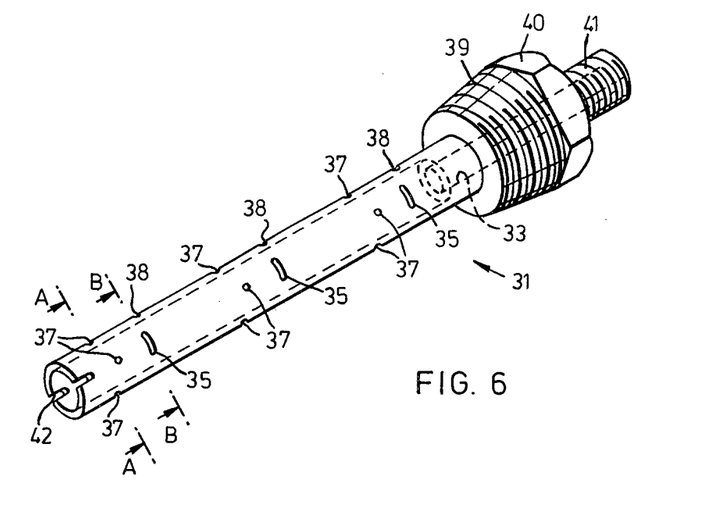
FIG. 6 is an isometric view of a body member of the device of FIG. 3.
Figure 7:
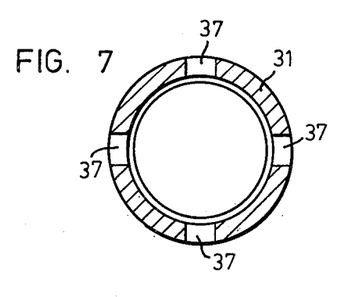
FIG. 7 is a radial cross-sectional view of the body member shown in FIG. 6, taken in the plane A—A of FIG. 6.
Figure 8:
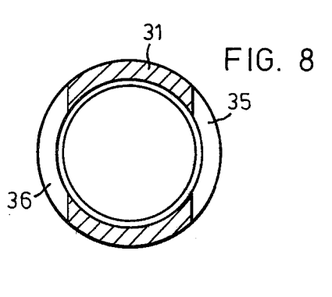
FIG. 8 is a radial cross-sectional view similar to that of FIG. 7 but taken in the plane B—B of FIG. 6.

The features of the body 31 described above are also shown in FIGS. 6, 7 and 8.

Figure 5:
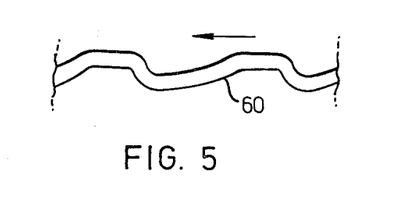
FIG. 5 shows a typical cam profile groove formed in a sleeve of the device of FIGS. 3 and 4.
Figure 9:
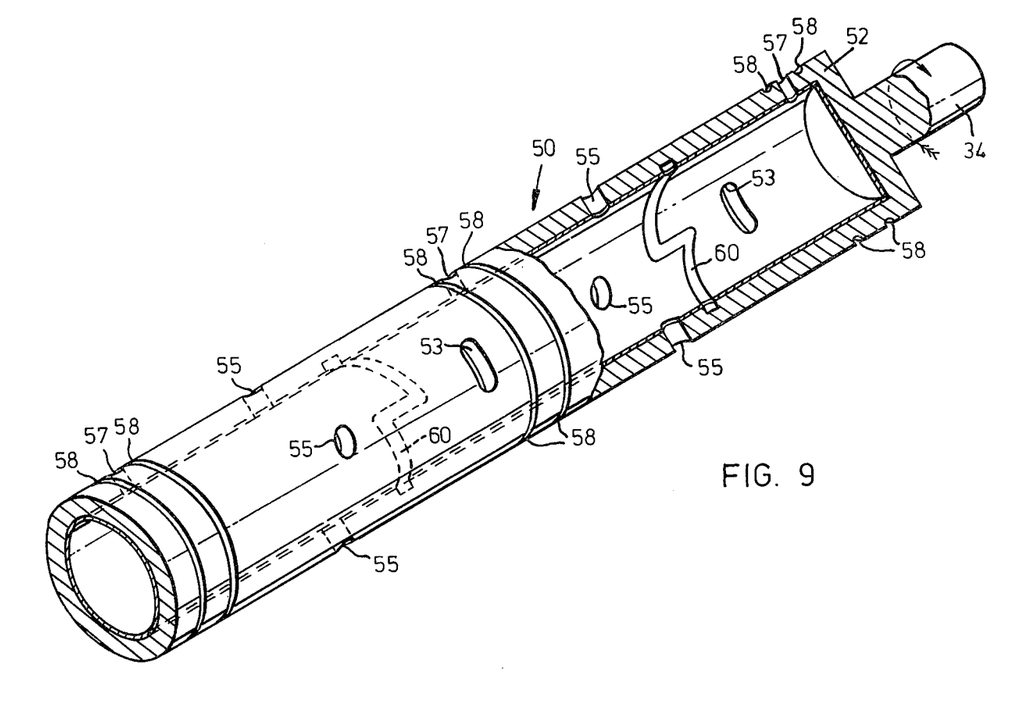
FIG. 9 is an axial cross-sectional isometric view of part of the sleeve.

Referring again to FIG. 4 and also to FIGS. 5 and 9, there is shown a cylindrical sleeve 50 which is closely received in the body 31. The sleeve 50 has a hollow, cylindrical interior, and is open at one end 51 and closed at the other end 52. The drive shaft 34 is coaxially attached to the closed end 52 of the sleeve 50, and along the length of the sleeve are provided sets of holes, each comprising a sample discharge port 57, a pair of diametrically disposed sample entry and exit ports 53, 54, and a pair of diametrically disposed fluid inlet and outlet orifices 55. As will be seen from FIG. 4, the spacing of the various holes in each set is such that when the closed end 52 of the sleeve abuts via a bearing 58 and thrust washer 59' against the closed end of the body 31, corresponding parts in the sleeve and the body register with each other when the sleeve 50 is rotated in the body.

On each axial side of each sample discharge port 57, the sleeve is formed with a suitably shaped circumferential groove 58 to receive an O-ring seal 59 (FIG. 4) so that a fluid sample discharged from the interior of the sleeve 50 via a discharge port 57 cannot leak between the sleeve and the body 31, and will be substantially wholly discharged via port 38 in the body 31.

Between the radial planes of the ports 55 and adjacent ports 53, 54, there are formed around the interior surface of the sleeve 50 cam profile grooves 60, the general form of which will be appreciated from FIG. 5 and FIG. 9. Roughly speaking, the form of the grooves 60 corresponds to cycle comprising a dwell period followed by a relatively rapid movement period, followed by a dwell and finally a relatively less rapid recovery movement.

The interior of the sleeve 50 is lined or coated with a wear resisting and/or lubricating material such as that known by its registered Trade Mark "Teflon".

Reference is now made to FIGS. 4, 5, 10, 11, 12, 13, 14 and 15.

Received closely within the sleeve 50 is a stack of components arranged end-to-end and comprising sample receptacles each in the form of a cylinder 70 alternating with spacers 90. The first and last axial components of the stack are cylinders 70.

The cylinder 70 at the closed end of the sleeve 50 has a smooth outer radial face 71 and rotatably abuts against the closed axial end of the sleeve 50. It is otherwise similar to the other cylinders 70 and as will be seen from FIGS. 10 and 11, each cylinder 70 has at its closed end an axial bore 72 which communicates with a radial bore 73 terminating in a port 74 for the discharge of fluid samples from the interior of the cylinder, and in addition sample entry and exit ports 75, cam follower slots 76 and fluid inlet and outlet orifices 77.

Figure 10:
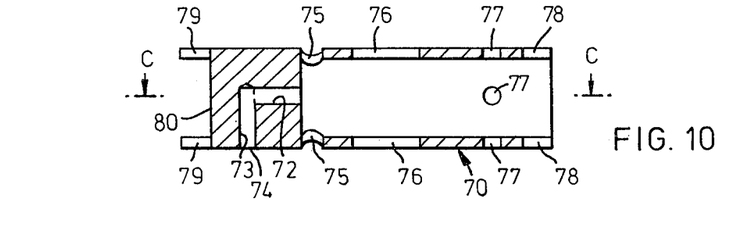
FIG. 10 is an axial cross-sectional elevation of a sample receptacle used in the device of FIGS. 3 and 4.
Figure 11:
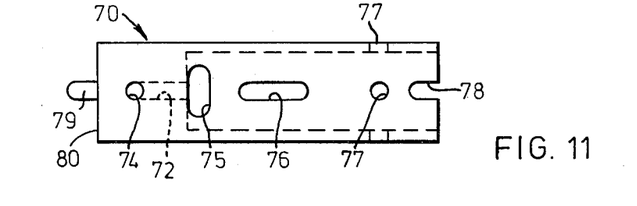
FIG. 11 is an axial cross-sectional view on plane C—C of FIG. 10.
Figure 12:
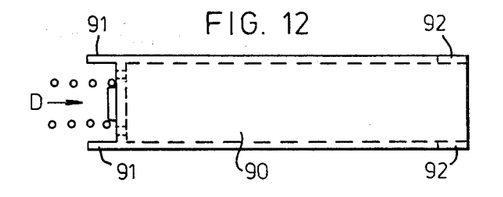
FIG. 12 is a side view of a spacer used in the device of FIGS. 3 and 4.
Figure 13:
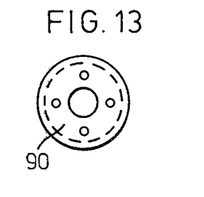
FIG. 13 is an end view of the spacer of FIG. 12 looking in the direction of the arrow D.
Figure 14:
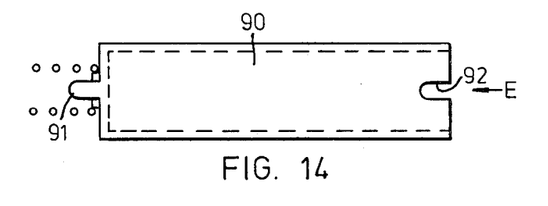
FIG. 14 is an underneath view of the spacer of FIG. 12.
Figure 15:
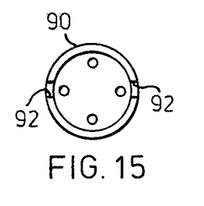
FIG. 15 is an end view of the spacer of FIG. 14 looking in the direction of arrow E.
Figure 16A:
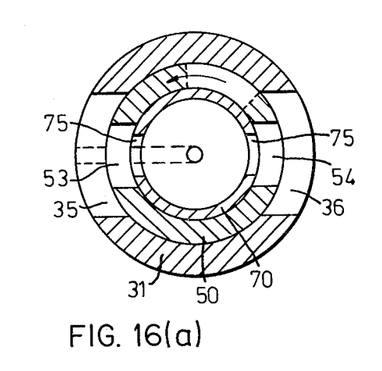
FIG. 16(a)–16(d) shows four diagrammatic radial cross-sectional elevations of the device of FIGS. 3 and 4 illustrating different stages of operation of the device.
Figure 16B:
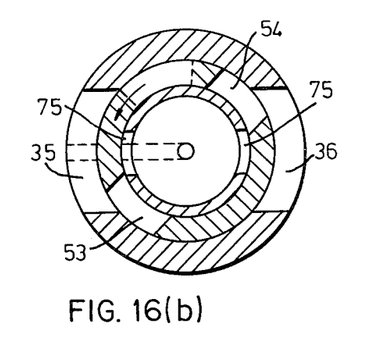
Figure 16C:
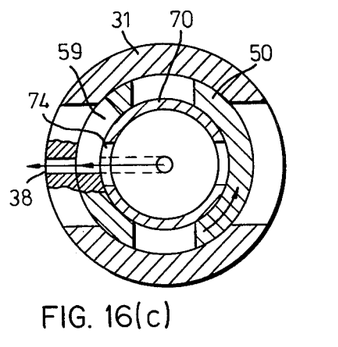
Figure 16D:
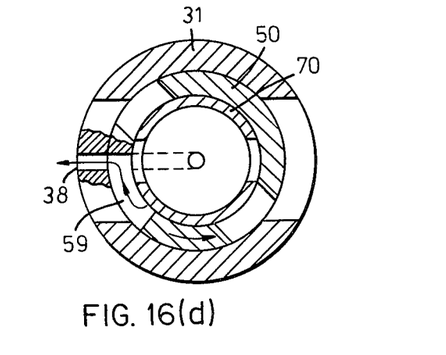

The edge of each cylinder 70 at the open end has a pair of diametrically disposed slots 78 formed therein to receive a retaining lug 91 on one end of a spacer 90 which is pressed against the open end of the cylinder in the stack. The other end of each spacer 90 is formed with a pair of diametrically disposed slots 92 to receive retaining lugs 79 provided on the outer radial face 80 at the closed end of each cylinder 70, apart from the cylinder which abuts the closed end 52 of the sleeve 50, and the cylinder 70 at the other end of the sleeve 50. The slots 78 of the latter cylinder receive lugs 101 of the key member 43 mentioned above.

The key member 43 comprises a circular disc-shaped thrust plate 102 which is freely received within the open end 32 of the body 31 with the lugs 101 extending radially from the edge thereof for receipt by the slots 42 in the edge of the body 31. A spring locating ring 103 is provided on one face of the plate 102 and a stud 104 extends from the ring 103 in the direction of the said stack of components. The end part 105 of the stud is of square cross-section and an aligning disc 106 having a square hole is freely received thereon within the open end of the sleeve 50. The forward face of the aligning disc 106 has lugs (not indicated) which are received in the slots 101 of the cylinder 70 adjacent to the open end 51 of the sleeve 50. A relatively strong spring 107 is disposed in compression between the plate 102 and the disc 106, and a spring retaining ring 107 partly received in a groove (not indicated) at the open end of the body 31 engages with the rear face of the thrust plate 102 to maintain the latter and all the components of the stack in relative abutment within the sleeve 50. It will be appreciated that the key member 43 enables the shaft 34 to rotate the sleeve 50 without causing rotation of the body 31 or the stack of components within the sleeve 50. It will also be appreciated that under the influence of the spring 107, the stack of components is strongly urged in the direction of the closed end of the sleeve 50.

The dimensions of the cylinders 70 and spacers 90 are such that on suitable relative rotation of the cylinders, the sleeve 50 and the body 31, the discharge ports 74 of the cylinders register with the discharge ports 57 of the sleeve 50 and the discharge ports 38 of the body 31. Similarly, the sample entry and exit ports 75 of the cylinders can be rotated into register with the corresponding ports 53, 54 of the sleeve 50 and the ports 35, 36 of the body 31, and the fluid inlet and outlet orifices 77 of the cylinders can be brought into register with the corresponding ports 55 of the sleeve 50 and 37 of the body 31. The cylinders 70 are so arranged relative to the body 31 that the sample discharge ports, the sample entry and exit ports and the fluid inlet and outlet orifices of the cylinders and the body are permanently in register, and that flow through the various ports and orifices is regulated by the rotation of the sleeve 50.

Within each cylinder 70 is a cylindrical piston 120 having a diametric hole therethrough in which is received a cam follower pin 121. The ends of each pin 121 project radially into a respective cam profile groove 60, the sides of which engage the pin 121. Each pin 121 is retained in the respective piston 120 by a spring urged ball catch 122 which registers in a central groove of the pin.

On rotation of the shaft 34, the rotation of the sleeve 50 causes the pin 121 to execute linear motion according to the profile of the sides of the cam profile groove 60, and the piston 120 is thereby also caused to execute the same linear motion. In contrast to the possibilities afforded by the prior art samplers of UK Pat. No. 1,025,905 and modifications thereof described above, the motion of the pistons 120 is substantially independent of the nature of the fluid being sampled and substantially independent of the rate of rotation of the shaft 34 because the position of the pistons is dictated by the mechanical cooperation of the cam follower pins 121 and the cam profile grooves 60.

The arrangement of the grooves 60 is (in preferred embodiments) such that all the pistons 120 are at substantially the same positions and moving with the same velocities in their respective cylinders 70 at every instant, and for each piston 120, the profile of the respective groove 60 is preferably such that the piston is stationary or moving relatively slowly when the sample inlet and exit ports of the body, sleeve and cylinder are at least partially in register so as to avoid an excessive sucking effect on fluid in the vicinity of the inlet and exit ports and so that, as far as the design of the sampler permits, the fluid within each cylinder is a representative sample of the fluid outside the sampler in the vicinity of the inlet and exit ports. On rotation of the sleeve 50, a sample of fluid within the cylinder is isolated when the ports 53, 54 of the sleeve are no longer in register with the inlet and exit ports of the body and the cylinder. The form of the cam profile grooves 60 is such that after the inlet and exit ports are out of register, as described above, the pistons are caused to move towards the closed ends of the cylinders, and the relative disposition of the grooves 60 and the ports in the sleeve 50 is such that the movement of the pistons towards the closed ends of the cylinders 70 only takes place when the sample discharge ports 74 thereof are in register with the sample discharge ports 57 of the sleeve 50 and the sample discharge ports 38 of the body 31. When the pistons 120 have been moved to the top of their stroke by the interaction of the cam follower pins 121 and the cam grooves 60, they are maintained at that position by dwell portions of the cam grooves 60 until the sleeve has rotated to bring subsequent sample inlet and outlet ports 53, 54 into register with the corresponding ports 75 of the cylinders 70 and 35, 36 of the body, whereupon the pistons are caused to return to the bottom of their strokes, where they may be stationary or moving relatively slowly with the inlet and exit ports open for a throughflow of fluid and the commencement of another cycle.

The pressure equalization ports 37 allow fluid to pass into and out of the cylinders behind the pistons to reduce the stress on the cam follower pins 121 and grooves 60.

As shown in FIG. 4, a spring is provided under relatively light compression between the rear face of each piston and the front face of the adjacent spacer 80 to reduce or eliminate relative movements of the components of the stack of components due to fluid pressure variations in the sampler during operation thereof.

FIG. 16 shows diagrammatically and schematically four parts of the operating cycle of the sampler of the invention, diagrams (a) and (b) being mainly in the radial plane of the sample inlet ports, and diagrams (c) and (d) being mainly in the radial plane of the sample discharge ports. In diagram (a), a sample of fluid is passing through the cylinder. In diagram (b), the rotation of the sleeve 50 has isolated a fluid sample in the cylinder. In diagram (c), the discharge ports are aligned to permit the discharge of the fluid sample, and in diagram (d), the discharge of the fluid sample has just finished.

Reference is now made to FIG. 3 wherein there are diagrammatically indicated fluid sample conduits 130, 131, 132, 133 connected to the body 31 for receiving fluid samples discharged from the ports 35 of the body. The conduits are connected to respective valves 134 for passing the samples together or separately to sample collection bottles (not shown).

Figure 17:
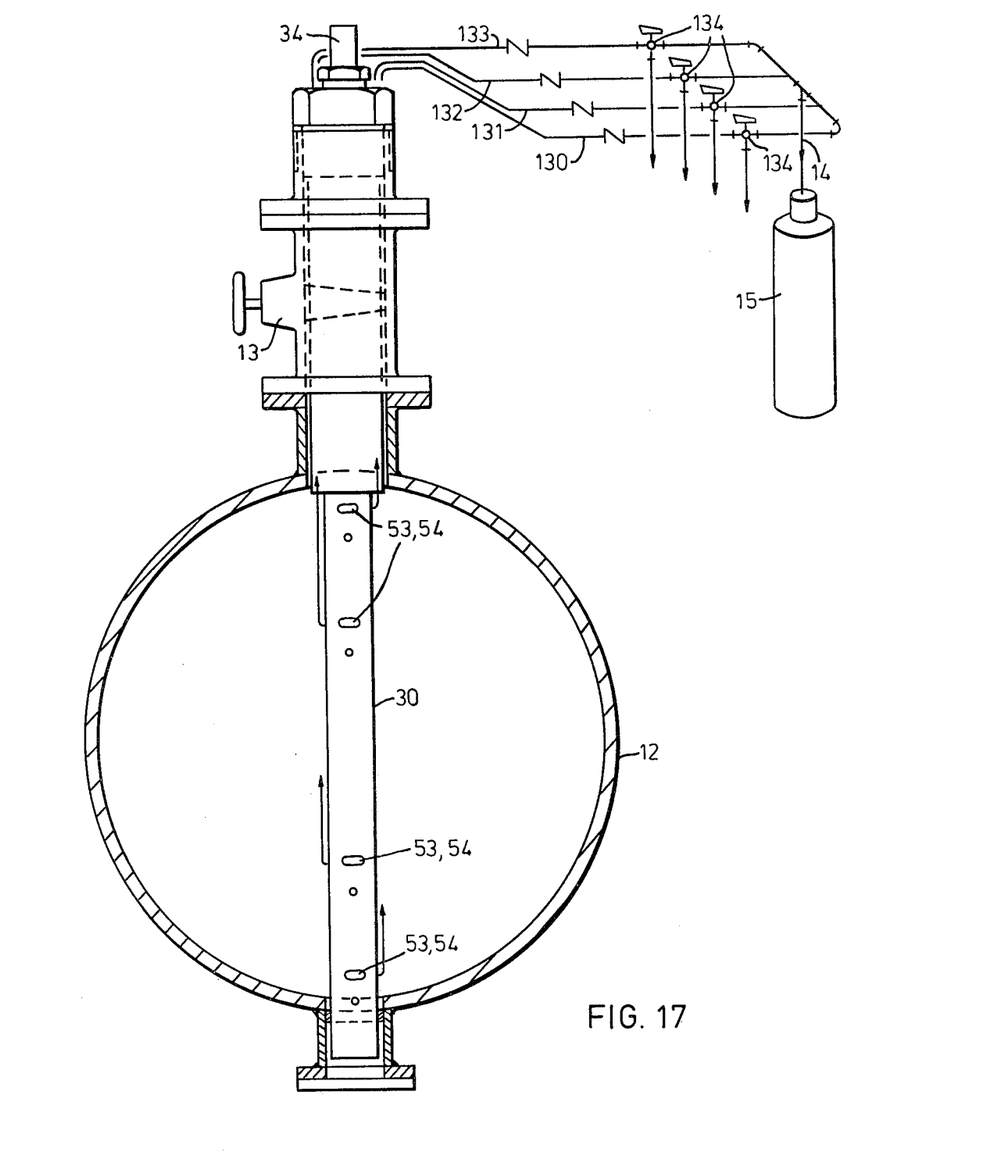
FIG. 17 shows, diagrammatically, a radial cross-section through a pipeline in which the device is installed.

FIG. 17 shows a multi-port sampler 30 of the type described in relation to FIGS. 3 and 4 installed in a pipeline 12 via a gate valve 13. The sample entrance and exit ports 53, 54 are disposed at locations which, by mathematical criteria, should give representative samples, despite the small number of sampling ports and the small volume of each sample. Preferably, the relative locations of the sampling ports is in accordance with the Chebyshef averaging method as described in the report entitled "Fluid Meters" by the American Society of Mechanical Engineers, Research Committee on Fluid Meters, edited by H. S. Bean, 6th Edition, 1971. Alternatively other averaging techniques may be employed, e.g. those known in the art by the names: "Equal Area", Newton-Cotes, Gauss, inter-alia. For particular types of sample averaging techniques, the spacings of the pistons may be non-uniform, and the displacements of different pistons may be different so that one cylinder will provide samples of larger volume than one or more other cylinder(s). Some of the reference numerals in FIG. 17 are in common with those of FIG. 1.

Figure 18:
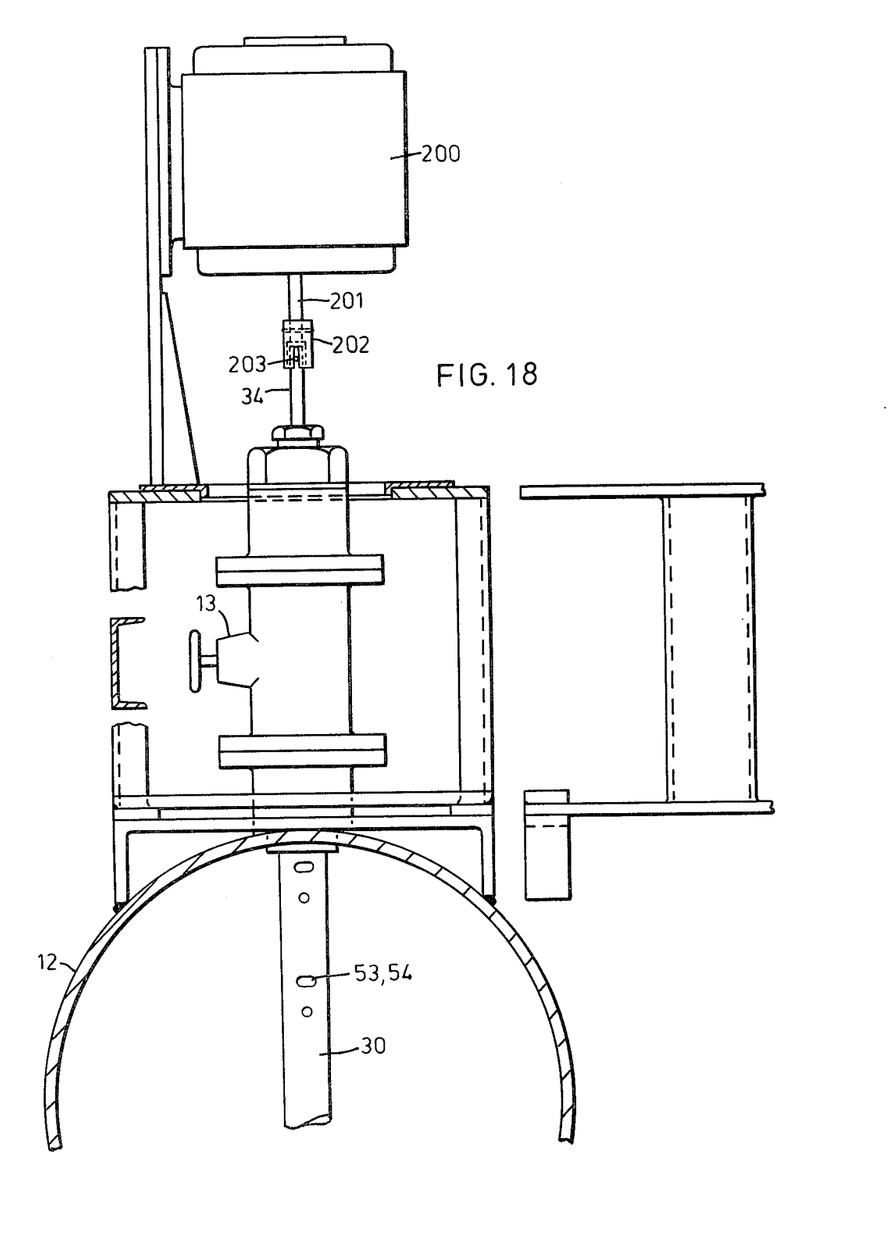
FIG. 18 is a view similar to FIG. 17 showing a drive arrangement.

In FIG. 18, there is depicted a direct drive for shaft 34 from an electric motor 200 mounted above the shaft. The drive spindle 201 of the motor 200 has a hollow collar 202 attached at its end and protruding therebeyond. The protruding part of the collar is split and receives and engages a drive pin 203 passed radially through the shaft 34, and the pin 203 is preferably about half way between the free end of the collar 202 and its closed end, thereby permitting a limited amount of vertical and tilt adjustment to take place.

I claim:

1. A fluid sampling device which, when assembled, comprises: a cylindrical sample receptacle having one end closed and the other end open, a sample entrance port in the cylindrical side of the receptacle, a sample discharge port for the discharge of samples of fluid from the interior of the receptacle; a piston reciprocable in the receptacle; a cam follower associated with the piston so that the follower and the piston move together, the cam follower having a part protruding through a slot in the cylindrical wall of the receptacle; a cylindrical sleeve in which the receptacle is received for relative rotation of the receptacle and sleeve; the sleeve having a sample entrance port which is arranged to be fully in register with the sample entrance port of the receptacle at a selected relative rotational position of the sleeve and the receptacle; the sleeve having an internal cam profile groove in which the protruding part of the cam follower is received and engaged by the sides of the groove to cause reciprocation of the piston in the receptacle during relative rotation of the sleeve and receptacle; a hollow body in which the cylindrical sleeve is received for relative rotation between the sleeve and the body; the body having a sample entrance port which is arranged to be fully in register with the sample entrance ports of the sleeve and the receptacle at a selected relative rotational position thereof; and means preventing relative rotation between the hollow body and the receptacle; the arrangement and construction of the device being such that the said sample entrance ports are fully in register when the piston is positioned by the engagement of the follower and the cam profile groove substantially at the bottom of its reciprocating stroke relative to the position of the samle discharge port, and such that at least the sample entrance ports of the receptacle and sleeve are fully out of register when the piston is positioned nearer to the sample discharge port than the bottom of its reciprocating stroke, whereby on relative rotation of the sleeve and the receptacle, the movement of the piston towards the top of its stroke causes any contents of the receptacle to be expelled via the sample discharge port.

2. A device according to claim 1 in which the receptacle, sleeve and body each have an exit port formed substantially diametrically opposite the respective sample entrance ports whereby when said sample entrance ports are all at least partially in register with each other, fluid outside the device can pass into the receptacle through the sample entrance ports and then out via the exit ports, whereby the composition of fluid in the receptacle is substantially identical with the fluid outside the device in the vicinity of the entrance and exit ports.

3. A device as in claim 1 in which the receptacle, sleeve and body each have an exit port formed substantially diametrically opposite the respective sample entrance ports whereby when said sample entrance ports are all at least partially in register with each other, fluid outside the device can pass into the receptacle through the sample entrance ports and then out via the exit ports, whereby the composition of fluid in the receptacle is substantially identical with the fluid outside the device in the vicinity of the entrance and exit ports and in which the sample discharge port is at the end of a radial bore in the cylindrical sample receptacle, and the sleeve and body have corresponding sample discharge orifices which are arranged to be in register with the sample discharge port when the position of the cam follower in the cam groove corresponds with that of the piston moving from the bottom to the top of its stroke.

4. A device as in claim 3 comprising a duct for receiving samples discharged from the sample discharge port via the said sample discharge orifices.

5. A device as in claim 1 in which the receptacle, sleeve and body each have an exit port formed substantially diametrically opposite the respective sample entrance ports whereby when said sample entrance ports are all at least partially in register with each other, fluid outside the device can pass into the receptacle through the sample entrance ports and then out via the exit ports, whereby the composition of fluid in the receptacle is substantially identical with the fluid outside the device in the vicinity of the entrance and exit ports and in which the sample discharge port is at the end of a radial bore in the cylindrical sample receptacle, and the sleeve and body have corresponding sample discharge orifices which are arranged to be in register with the sample discharge port when the position of the cam follower in the cam groove corresponds with that of the piston moving from the bottom to the top of its stroke and in which the form of the cam groove is such that the piston is substantially stationary at, or moving relatively slowly towards, the bottom of its stroke when the sample entrance ports of the receptacle, sleeve and body are all at least partly in register with each other, and comprising a duct for receiving samples discharged from the sample discharge port via the said sample discharge orifices.

6. A device as in claim 1 having at least one orifice to permit the ingress and egress of fluid behind the piston during movement thereof.

7. A device as in claim 5 having at least one orifice to permit the ingress and egress of fluid behind the piston during movement thereof.

8. A device as in claim 1 comprising a plurality of similar cylindrical sample receptacles co-axially received as a stack within the sleeve and rotationally fixed relative to each other, each receptacle having a piston reciprocable therein and each piston having associated therewith a cam follower whereof a part protrudes through a respective slot in the cylindrical wall of the receptacle and is engaged against the sides of a respective cam profile groove whose form is such as to cause reciprocation of the respective piston in the receptacle on relative rotation of the sleeve and receptacles, each receptacle having a sample entrance port corresponding with the sample entrance port of each receptacle, the sleeve and receptacles being co-axially received in the body, the body having a sample entrance port corresponding with the sample entrance port of each receptacle, the body and sleeve being arranged for relative rotation and there being means preventing relative rotation between the body and the receptacles, there being sample discharge ports for the discharge of samples from each receptacle and respective corresponding sample discharge orifices in the sleeve and body, the construction and arrangement of the device being such that for each receptacle, the cam follower and cam profile groove maintain the piston at the bottom of its stroke when the corresponding sample entrance ports of the receptacle, sleeve and body are all at least partly in register with each other, and cause the piston to move towards the top of its stroke when the corresponding discharge orifices are at least partly in register with each other.

9. A device as in claim 8 in which the profiles of the cam grooves are of such form that the piston in each receptacle is substantially in the same position in its working cycle as the piston in every other receptacle.

10. A device as in claim 8 comprising respective ducts for receiving samples discharged from each of the sample discharge ports.

11. A device as in claim 9 comprising respective ducts for receiving samples discharged from each of the sample discharge ports.

12. A device as in claim 8 comprising a spacing member between and abutted by two axially separated receptacles, each spacing member having a lug at one axial end which is received in a corresponding recess in an abutting receptacle to prevent relative rotation therebetween.

13. A device as in claim 12 in which the other axial end of the spacing member has a recess in which a lug of an abutting receptacle is received to prevent relative rotation of the spacing member and receptacle.

14. A device as in claim 13 comprising spring means which biasses all said receptacles towards one axial end of the sleeve.

15. A device as in claim 12 comprising spring means which biasses all said receptacles towards one axial end of the sleeve.

16. A device as in claim 15 in which said means preventing relative rotation of the body and the receptacles comprises a keying member which connects one axial end of the body and an adjacent part of the receptacle at that axial end of the device.

17. A device as in claim 16 comprising spring means which biasses all said receptacles towards one axial end of the sleeve in which the keying member comprises a thrust plate member, and in which the spring means is maintained in compression between the thrust plate member and the receptacle at the opposite axial end of the sleeve.

18. A device as in claim 17 in which the sample entrance ports are located along the length of the device with a spacing in accordance with a mathematical samples' averaging technique.

19. A device as in claim 17 comprising a shaft attached to the sleeve and having a part protruding through an axial end of the body for attachment to means for rotating the shaft.

20. A pipeline or container in which a device as in claim 19 is installed including means connected to said shaft for rotating said sleeve.

* * * * *